US011241216B2

(12) United States Patent
Kurita

(10) Patent No.: US 11,241,216 B2
(45) Date of Patent: Feb. 8, 2022

(54) METHOD OF CONTROLLING PORTABLE INFORMATION TERMINAL AND MEDICAL DIAGNOSTIC IMAGING APPARATUS

(71) Applicant: Toshiba Medical Systems Corporation, Otawara (JP)

(72) Inventor: Koichiro Kurita, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 15/261,314

(22) Filed: Sep. 9, 2016

(65) Prior Publication Data
US 2017/0065361 A1 Mar. 9, 2017

(30) Foreign Application Priority Data

Sep. 9, 2015 (JP) .............................. JP2015-177791
Aug. 19, 2016 (JP) .............................. JP2016-161094

(51) Int. Cl.
*G06F 3/0481* (2013.01)
*A61B 8/00* (2006.01)
(Continued)

(52) U.S. Cl.
CPC ............ *A61B 8/4427* (2013.01); *A61B 5/026* (2013.01); *A61B 5/055* (2013.01); *A61B 8/4411* (2013.01);
(Continued)

(58) Field of Classification Search
CPC ...... G06F 9/543; G06F 3/0481; G06F 3/0484; G06F 21/31; G06F 9/541; G06F 9/451;
(Continued)

(56) References Cited

U.S. PATENT DOCUMENTS 6,353,445 B1 * 3/2002 Babula ................. A61B 5/0002
715/733
6,614,422 B1 * 9/2003 Rafii ..................... G06F 1/1626
345/168

(Continued)

FOREIGN PATENT DOCUMENTS

JP H03-141935 A 6/1991
JP 2007-117383 5/2007
(Continued)

OTHER PUBLICATIONS

Japanese Office Action dated May 19, 2020, issued in Japanese Patent Application No. 2016-161094.

*Primary Examiner* — Steven P Sax
(74) *Attorney, Agent, or Firm* — Oblon, McClelland, Maier & Neustadt, L.L.P.

(57) ABSTRACT

A method of controlling a portable information terminal comprises causing the portable information terminal to display first operation screen data which is obtained by wireless communication with a medical diagnostic imaging apparatus and includes graphic data for reception of an operation from an operator and second operation screen data which is read to the portable information terminal and includes graphic data for reception of an operation from the operator, and causing the portable information terminal to generate, in accordance with the operations for the displayed first operation screen data and the displayed second operation screen data, a command signal for causing the medical diagnostic imaging apparatus to execute functions corresponding to the operations.

8 Claims, 9 Drawing Sheets

(51) Int. Cl.
*A61B 5/055* (2006.01)
*G06F 3/0488* (2013.01)
*A61B 5/026* (2006.01)
*G06F 3/0484* (2013.01)
*G06F 3/14* (2006.01)

(52) U.S. Cl.
CPC ........ *G06F 3/0488* (2013.01); *G06F 3/04845* (2013.01); *G06F 3/04886* (2013.01); *G06F 3/14* (2013.01); *A61B 8/462* (2013.01); *A61B 8/54* (2013.01); *G06F 3/1423* (2013.01); *G06F 3/1454* (2013.01); *G09G 2340/02* (2013.01); *G09G 2340/0435* (2013.01); *G09G 2350/00* (2013.01); *G09G 2370/16* (2013.01)

(58) Field of Classification Search
CPC .. G06F 40/106; G06F 21/105; G06F 3/04886; G06F 3/0488; G06F 3/04845; G06F 3/014; G06F 3/1423; G06F 3/1454; G09G 2340/145; G09G 2370/16; G09G 2340/0435; G09G 2340/02; G09G 2350/00; H04N 19/40; A61B 8/4427; A61B 5/055; A61B 5/026; A61B 8/4411; A61B 8/462; A61B 8/54
See application file for complete search history.

(56) References Cited

U.S. PATENT DOCUMENTS

| | | | | |
|---|---|---|---|---|
| 6,747,561 B1* | 6/2004 | Reeves | | G06F 1/1626 340/573.1 |
| 7,263,710 B1* | 8/2007 | Hummel, Jr. | | G06F 19/324 725/86 |
| 7,778,848 B1* | 8/2010 | Reeves | | G06Q 50/22 705/3 |
| 8,423,387 B1* | 4/2013 | Mirza | | G06F 19/3418 705/3 |
| 8,568,319 B1* | 10/2013 | Kaplan | | A61B 8/4483 600/437 |
| 9,671,941 B1* | 6/2017 | Gray | | G06F 3/016 |
| 10,120,839 B2* | 11/2018 | Long | | G06F 40/106 |
| 2002/0095424 A1* | 7/2002 | Chung | | G16H 10/60 |
| 2006/0020206 A1* | 1/2006 | Serra | | A61B 8/465 600/447 |
| 2007/0066911 A1* | 3/2007 | Klingenbeck-Regn | | A61B 5/02028 600/523 |
| 2008/0021834 A1* | 1/2008 | Holla | | G06F 19/322 705/51 |
| 2008/0072151 A1* | 3/2008 | Song | | G06F 3/0481 715/708 |
| 2009/0034688 A1* | 2/2009 | Koren | | A61B 6/4233 378/198 |
| 2010/0121157 A1* | 5/2010 | Espina | | A61B 5/411 600/301 |
| 2011/0085778 A1* | 4/2011 | Iwase | | H04N 5/232935 386/228 |
| 2011/0112399 A1* | 5/2011 | Willems | | G01S 7/52079 600/437 |
| 2011/0208534 A1* | 8/2011 | Liotta | | G16H 20/10 705/2 |
| 2011/0208541 A1* | 8/2011 | Wilson | | A61G 12/00 705/3 |
| 2012/0148031 A1* | 6/2012 | Eaves | | A61B 6/4405 378/198 |
| 2013/0054467 A1* | 2/2013 | Dala | | G06F 19/3418 705/51 |
| 2013/0167242 A1* | 6/2013 | Paliwal | | G06F 21/105 726/26 |
| 2013/0219072 A1* | 8/2013 | Han | | H04L 65/602 709/228 |
| 2013/0253325 A1* | 9/2013 | Call | | A61B 8/5246 600/447 |
| 2013/0257729 A1* | 10/2013 | Edwards | | G06F 3/044 345/163 |
| 2013/0314386 A1* | 11/2013 | Han | | G09G 3/00 345/204 |
| 2013/0326397 A1* | 12/2013 | Kim | | G06F 3/1454 715/781 |
| 2014/0005550 A1* | 1/2014 | Lu | | A61B 8/4245 600/459 |
| 2014/0039277 A1* | 2/2014 | Abraham | | A61B 8/4483 600/301 |
| 2014/0044201 A1* | 2/2014 | Carnes | | H04L 27/0008 375/259 |
| 2014/0053111 A1* | 2/2014 | Beckman | | G06F 3/14 715/856 |
| 2014/0289747 A1* | 9/2014 | Kukulski | | G06F 9/541 719/319 |
| 2014/0340204 A1* | 11/2014 | O'Shea | | G08C 17/02 340/12.54 |
| 2015/0085986 A1* | 3/2015 | Dinse | | A61B 6/10 378/98 |
| 2015/0182197 A1* | 7/2015 | Willems | | A61B 8/462 600/443 |
| 2015/0195147 A1* | 7/2015 | Jee | | H04W 76/23 715/740 |
| 2015/0278895 A1* | 10/2015 | Joy | | G07G 1/01 705/21 |
| 2015/0324080 A1* | 11/2015 | Jin | | G06F 3/0485 715/784 |
| 2016/0011290 A1* | 1/2016 | Iannello | | G01R 33/56527 600/309 |
| 2016/0029890 A1* | 2/2016 | Stump | | G16H 50/30 600/301 |
| 2016/0049064 A1* | 2/2016 | McNabb | | G08B 21/10 340/540 |
| 2016/0081662 A1* | 3/2016 | Denk | | A61B 8/54 600/437 |
| 2016/0196054 A1* | 7/2016 | Perez-Feliciano | | G06F 9/451 715/829 |
| 2017/0071565 A1* | 3/2017 | Kahya | | G16H 40/63 |

FOREIGN PATENT DOCUMENTS

| | | |
|---|---|---|
| JP | 2010-82268 | 4/2010 |
| JP | 5331431 | 10/2013 |
| JP | 2015-100404 A | 6/2015 |
| WO | WO 2013/081042 A1 | 6/2013 |

* cited by examiner

METHOD OF CONTROLLING PORTABLE INFORMATION TERMINAL AND MEDICAL DIAGNOSTIC IMAGING APPARATUS

CROSS-REFERENCE TO RELATED APPLICATIONS

This application is based upon and claims the benefit of priority from the prior Japanese Patent Application No. 2015-177791, filed Sep. 9, 2015 and No. 2016-161094, filed Aug. 19, 2016, the entire contents of both which are incorporated herein by reference.

FIELD

Embodiments described herein relate generally to a method of controlling a portable information terminal and a medical diagnostic imaging apparatus.

BACKGROUND

Medical diagnostic imaging apparatuses are designed to visualize the insides of objects by various types of techniques, and include various types of modalities such as X-ray CT apparatuses, magnetic resonance imaging apparatuses, X-ray diagnostic apparatuses, and ultrasound diagnostic apparatuses. For example, an ultrasound diagnostic apparatus radiates ultrasound pulses generated from transducers provided in an ultrasound probe into an object and receives reflected ultrasound waves caused by the differences in acoustic impedance between object tissues via the transducers, thereby acquiring biological information. The operator can check in real time a moving image displayed on the monitor of the apparatus by only performing the simple operation of bringing the ultrasound probe into contact with the body surface.

When using the scan function of the ultrasound diagnostic apparatus, the operator scans an object by using the ultrasound probe while assuming various postures. For example, when scanning lower extremity blood vessels, the operator needs to assume a semi-crouching position and casts his/her eyes on a lower extremity portion to scan the lower extremity of an object. It is therefore difficult for the operator to directly operate the console. In addition, when the operator scans an object during a surgical operation, the object is located away from the console of the ultrasound diagnostic apparatus in consideration of the placement of surgical equipment. On the other hand, the operator scans the object by bringing the ultrasound probe close to the object during a surgical operation. This makes it difficult for the operator to directly operate the console of the ultrasound diagnostic apparatus.

DETAILED DESCRIPTION

According to one embodiment, a method of controlling a portable information terminal comprises causing the portable information terminal to display first operation screen data which is obtained by wireless communication with a medical diagnostic imaging apparatus and includes graphic data for reception of an operation from an operator and second operation screen data which is read to the portable information terminal and includes graphic data for reception of an operation from the operator, and causing the portable information terminal to generate, in accordance with the operations for the displayed first operation screen data and the displayed second operation screen data, a command signal for causing the medical diagnostic imaging apparatus to execute functions corresponding to the operations.

A medical diagnostic imaging apparatus according to this embodiment will be described below with reference to the accompanying drawing.

For a concrete description of the embodiment, assume that the medical diagnostic imaging apparatus is an ultrasound diagnostic apparatus using an ultrasound probe. Note that the medical diagnostic imaging apparatus may be any one of the following: an X-ray diagnostic apparatus, an X-ray CT apparatus, an MRI apparatus, and a nuclear medicine diagnostic apparatus.

Figure 1:
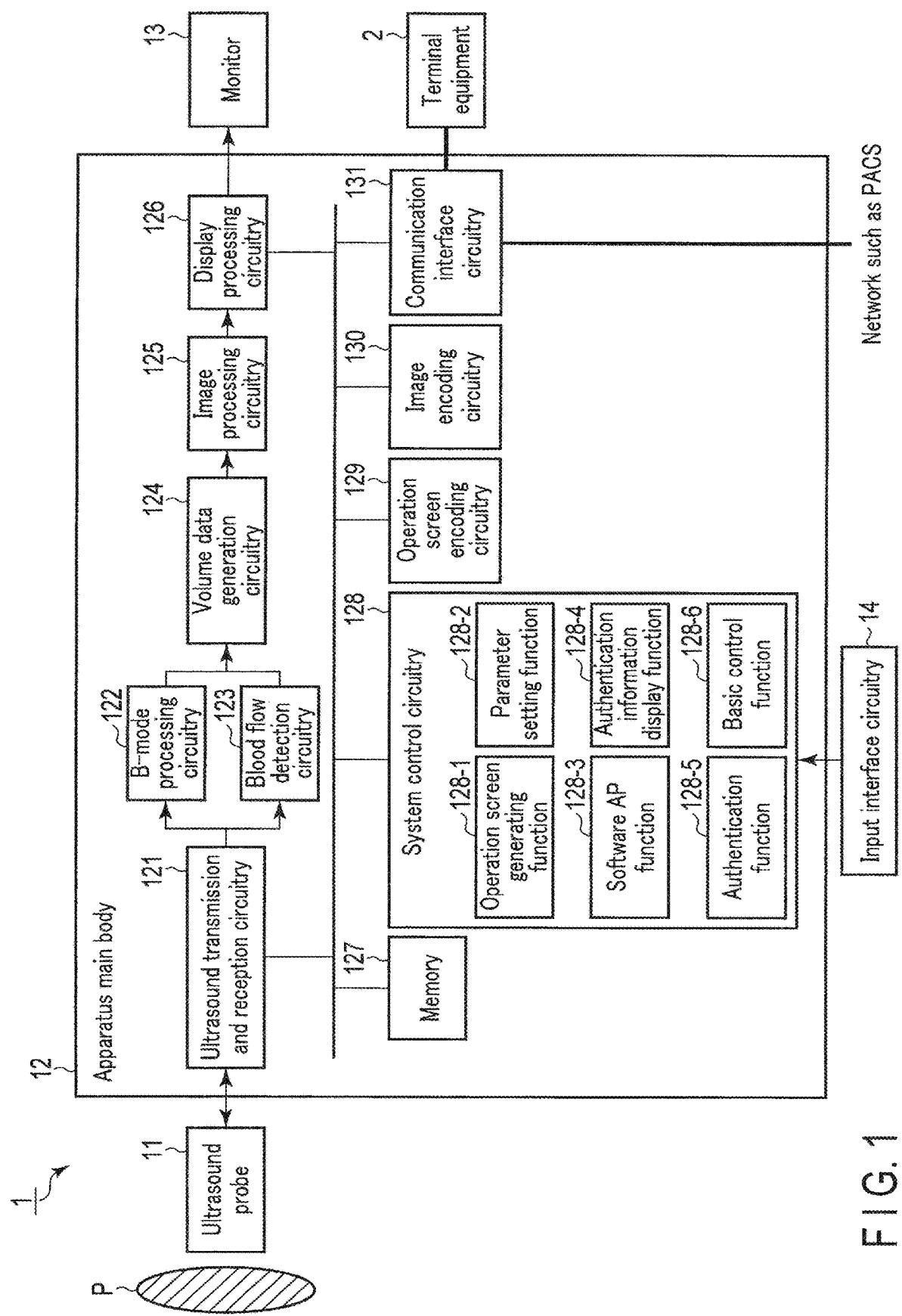
FIG. 1 is a block diagram showing the system arrangement of an ultrasound diagnostic system according to an embodiment.

FIG. 1 is a block diagram showing an example of the system arrangement of the ultrasound diagnostic system according to this embodiment. As shown in FIG. 1, the ultrasound diagnostic system includes an ultrasound diagnostic apparatus 1 and terminal equipment 2. The ultrasound diagnostic apparatus 1 and the terminal equipment 2 are wirelessly communicably connected to each other via a communication line. In addition, the ultrasound diagnostic apparatus 1 is wiredly communicably connected to a communication line different from that with the terminal equipment 2, for example, an in-hospital network. In this case, even if the traffic amount between the ultrasound diagnostic apparatus 1 and the in-hospital network increases, no limitation is imposed on communication resources which can use communication between the ultrasound diagnostic apparatus 1 and the terminal equipment 2. Note that the ultrasound diagnostic apparatus 1 may be wirelessly communicably connected to the in-hospital network.

The ultrasound diagnostic apparatus 1 includes an ultrasound probe 11, an apparatus main body 12, a monitor 13, and input interface circuitry 14. The apparatus main body 12 is communicably connected to the terminal equipment 2 via a communication line.

The ultrasound probe 11 is a device (probe) which transmits ultrasound waves to an object typified by a living body and receives reflected waves from the object based on the transmitted ultrasound waves. The ultrasound probe 11 has, on its distal end, an array of a plurality of piezoelectric transducers (ultrasound transducers), a matching layer, a backing member, and the like. The ultrasound probe 11 is a one-dimensional array probe having a plurality of ultrasound transducers arrayed along a predetermined direction.

The piezoelectric transducers transmit ultrasound waves in a desired direction in a scan area based on driving signals from ultrasound transmission and reception circuitry 121, and receive reflected waves from the object. The piezoelectric transducers convert the received reflected waves into electrical signals. The matching layer is an intermediate layer which is provided for the piezoelectric transducers to make ultrasound energy efficiently propagate. The backing member is provided on the opposite side to the matching layer so as to sandwich the piezoelectric transducers with the matching layer, and prevents ultrasound waves from propagating backward from the piezoelectric transducers.

When the ultrasound probe 11 transmits an ultrasound wave to an object, the transmitted ultrasound wave is sequentially reflected by a discontinuity surface of acoustic impedance of internal body tissue, and is received as an echo signal by the ultrasound probe 11. The amplitude of this echo signal depends on an acoustic impedance difference on the discontinuity surface by which the echo signal is reflected. The echo produced when a transmitted ultrasound pulse is reflected by a moving blood flow is subjected to a frequency shift depending on the velocity component of the moving body in the ultrasound transmission/reception direction due to the Doppler effect.

Note that in this embodiment, the ultrasound probe 11 is a one-dimensional array probe. However, this is not exhaustive, and the ultrasound probe 11 may be a two-dimensional array probe (i.e., a probe having ultrasound transducers arranged in the form of a two-dimensional matrix) or a mechanical 4D probe (i.e., a probe which can execute ultrasound scanning while mechanically swinging an ultrasound transducer array in a direction perpendicular to the array direction) as a probe which can acquire volume data.

The apparatus main body 12 includes the ultrasound transmission and reception circuitry 121, B-mode processing circuitry 122, blood flow detection circuitry 123, volume data generation circuitry 124, image processing circuitry 125, display processing circuitry 126, a memory 127, system control circuitry 128, operation screen encoding circuitry 129, image encoding circuitry 130, and communication interface circuitry 131. The ultrasound transmission and reception circuitry 121, the display processing circuitry 126, the memory 127, the system control circuitry 128, the operation screen encoding circuitry 129, the image encoding circuitry 130, and the communication interface circuitry 131 are connected to each other via a bus.

The ultrasound transmission and reception circuitry 121 includes trigger generation circuitry, delay circuitry, and pulser circuitry (none of which are shown). The trigger generation circuitry repeatedly generates trigger pulses for the formation of transmission ultrasound waves at a predetermined rate frequency fr Hz (period: 1/fr sec). The delay circuitry gives each trigger pulse a delay time necessary to focus an ultrasound wave into a beam and determine transmission directivity for each channel. The pulser circuitry applies a driving pulse to the ultrasound probe 11 at the timing based on this trigger pulse.

The ultrasound transmission and reception circuitry 121 includes amplifier circuitry, an A/D converter, delay circuitry, and an adder (none of which are shown). The amplifier circuitry amplifies an echo signal received via the ultrasound probe 11 for each channel. The A/D converter converts each amplified analog echo signal into a digital echo signal. The delay circuitry gives the digitally converted echo signals delay times necessary to determine reception directivities and perform reception dynamic focusing. The adder then performs, for each channel, addition processing for the digital echo signals which are phase-matched by the given delay times. With this addition, a reflection component from a direction corresponding to the reception directivity of the echo signal is enhanced to form a composite beam for ultrasound transmission/reception in accordance with reception directivity and transmission directivity.

The B-mode processing circuitry 122 is a processor which generates a plurality of B-mode data based on echo signals received from the ultrasound transmission and reception circuitry 121. The B-mode processing circuitry 122 receives echo signals from the ultrasound transmission and reception circuitry 121, and performs logarithmic amplification, envelope detection processing, and the like for the signals to generate a plurality of B-mode data whose signal intensities are expressed by luminance levels. The plurality of generated B-mode data are stored, in a RAW data memory (not shown), as B-mode RAW data which are B-mode data on three-dimensional ultrasound scanning lines.

The blood flow detection circuitry 123 is a processor which generates a plurality of blood flow data based on echo signals received from the ultrasound transmission and reception circuitry 121. The blood flow detection circuitry 123 extracts blood flow signals from the echo signals received from the ultrasound transmission and reception circuitry 121, and generates a plurality of blood flow data. The plurality of generated blood flow data are stored, in the RAW data memory (not shown), as blood flow RAW data which are blood flow data on three-dimensional ultrasound scanning lines. In general, the blood flow detection circuitry 123 extracts blood flows by CFM (Color Flow Mapping). In this case, the blood flow detection circuitry 123 analyzes the blood flow signals to obtain blood flow information such as mean velocities, variances, and powers as blood flow data at multiple points.

The volume data generation circuitry 124 is a processor which generates volume data based on RAW data stored in the RAW data memory.

The volume data generation circuitry 124 generates B-mode volume data by executing RAW-voxel conversion including interpolation processing with consideration given to spatial position information with respect to B-mode RAW data stored in the RAW data memory.

The volume data generation circuitry 124 generates blood flow volume data by executing RAW-voxel conversion including interpolation processing with consideration given to spatial position information with respect to blood flow RAW data stored in the RAW data memory.

The image processing circuitry 125 is a processor which generates various types of image data based on volume data received from the volume data generation circuitry 124. The image processing circuitry 125 performs predetermined image processing such as volume rendering, MPR (Multi Planar Reconstruction), and MIP (Maximum Intensity Projection) for the volume data received from the volume data generation circuitry 124. Note that for the purpose of reducing noise or improving smooth concatenation of images, a two-dimensional filter may be inserted after the image processing circuitry 125 to perform spatial smoothing.

The display processing circuitry 126 is a processor which generates ultrasound image data associated with ultrasound images to be displayed on the monitor 13 based on various types of image data generated/processed by the image processing circuitry 125. The display processing circuitry 126 executes various types of processing associated with a dynamic range, luminance (brightness), contrast, γ curve correction, RGB conversion, and the like for various types of image data generated/processed by the image processing circuitry 125. The display processing circuitry 126 generates ultrasound image data associated with ultrasound images to be displayed on the monitor 13 based on a preset resolution and display frame rate. The display frame rate is the number of display frames of ultrasound images generated per sec by the display processing circuitry 126. In general, the display frame rate is basically the same as an acoustic frame rate determined by a scan period with respect to an object with an ultrasound probe. Note that the display frame rate may be set to a fixed value such as 30 frames per sec.

The memory 127 includes a magnetic or optical recording medium or a processor-readable recording medium such as a semiconductor memory. The memory 127 saves programs for implementing an operation screen generating function 128-1, a parameter setting function 128-2, a SoftwareAP function 128-3, an authentication information display function 128-4, an authentication function 128-5, and a basic control function 128-6, diagnostic protocols, a data size per ultrasound image frame and display frame for the generation of ultrasound image data, transmission/reception conditions such as the compression ratio of ultrasound image data at the time of transfer of ultrasound image data from the ultrasound diagnostic apparatus 1 to the terminal equipment 2, and other data groups. Note that the compression ratio is set in advance to a predetermined value.

The memory 127 also stores a terminal display frame rate. The terminal display frame rate is the number of display frames per sec of ultrasound images displayed on the monitor of display circuitry 22 of the terminal equipment 2. Note that the terminal display frame rate is basically the same as the display frame rate.

In addition, the memory 127 stores an operation screen database. The operation screen database is an aggregate of data handling image data representing an operation screen used by an operator 3 to operate the ultrasound diagnostic apparatus 1 from the terminal equipment 2 and additional information of the image data as one logical record. An operation screen represented by image data is displayed on the touch panel of input interface circuitry 21 of the terminal equipment 2 (to be described later).

Image data representing an operation screen is generated in imitation of an operation screen displayed on the touch panel of the input interface circuitry 14 of the ultrasound diagnostic apparatus 1. Image data representing operation screens include image data for receiving an operation from the operator 3, for example, the image data of various types of patterns required for the operator 3 to operate the ultrasound diagnostic apparatus 1 from the terminal equipment 2. In addition, image data representing an operation screen includes image data representing at least one function button arrayed on an operation screen displayed on the touch panel of the input interface circuitry 14 of the ultrasound diagnostic apparatus 1. Image data representing a function button is image data for identifying a button for executing a specific function on the touch panel of the input interface circuitry 21 of the terminal equipment 2.

Additional information of image data representing an operation screen is information indicating a specific function to be executed when the user presses a coordinate area where, for example, a predetermined function button is arranged on the operation screen represented by the image data. That is, the additional information of image data representing an operation screen includes, for example, function information for the execution of predetermined processing and position information indicating a specific position on the operation screen at which a button corresponding to the function is arranged. The additional information of image data representing operation screens includes additional information of various patterns corresponding to image data representing operation screens.

As will be described later, image data representing an operation screen and the additional information of the image data are used by the ultrasound diagnostic apparatus 1 when the terminal equipment 2 notifies the ultrasound diagnostic apparatus 1 of a command signal.

In addition, an operation screen database is an aggregate of data handling image data representing an image of panel switches to be used by the operator 3 to operate the ultrasound diagnostic apparatus 1 from the terminal equipment 2 and additional information of the image data as one logical record. The panel switch image is displayed on the touch panel of the input interface circuitry 21 of the terminal equipment 2.

Image data representing a panel switch image is generated in imitation of the shape of panel switches of the input interface circuitry 14 of the ultrasound diagnostic apparatus 1. Panel switches are physical switches arranged on the front surface of the ultrasound diagnostic apparatus 1 to receive predetermined input operations from the operator 3. Image data representing a panel switch image includes image data representing at least one panel switch arranged on the front surface of the ultrasound diagnostic apparatus 1.

Additional information of image data representing panel switches is information indicating a specific function to be executed when the user presses a coordinate area where, for example, a predetermined icon is arranged on the operation screen represented by the image data. That is, the addition information of image data representing panel switches includes, for example, function information for the execution of predetermined processing and position information indicating a specific position on the operation screen at which a button corresponding to the function is arranged. The additional information of image data representing panel switches includes additional information of various patterns corresponding to image data representing panel switches.

Image data representing a panel switch image and the additional information of the image data are read from the memory 127 into the terminal equipment 2 when it is permitted to directly perform a predetermined remote operation concerning the ultrasound diagnostic apparatus 1 from the terminal equipment 2, as will be described later.

In addition, the memory 127 stores identifying information which is required when the authentication function 128-5 of the system control circuitry 128 (to be described later) checks whether a person who operates the ultrasound diagnostic apparatus 1 from the terminal equipment 2 has the corresponding authority. Identifying information is, for example, a password. Note that a password may be manually set or automatically generated in the ultrasound diagnostic apparatus 1. Alternatively, a password may be obtained from a predetermined external apparatus.

The system control circuitry 128 is, for example, a processor which controls each constituent circuitry of the ultrasound diagnostic apparatus 1. The system control circuitry 128 functions as the main unit of the ultrasound diagnostic apparatus 1. The system control circuitry 128 invokes operation programs from the memory 127 and execute the invoked programs to implement the operation screen generating function 128-1, the parameter setting function 128-2, the SoftwareAP function 128-3, the authentication information display function 128-4, the authentication function 128-5, and the basic control function 128-6.

The operation screen generating function 128-1 is a function of generating operation screen data to be transmitted to the terminal equipment 2. More specifically, with the operation screen generating function 128-1, the system control circuitry 128 receives a command signal from the terminal equipment 2 via the communication interface circuitry 131. The command signal is a signal for instructing to change the operation screen displayed on the touch panel of the input interface circuitry 21 of the terminal equipment 2 (to be described later) to a predetermined operation screen. The command signal includes information representing an operation screen after the change. As will be described later, when the operator 3 presses a predetermined button on the touch panel of the input interface circuitry 21 of the terminal equipment 2, system control circuitry 24 of the terminal equipment 2 refers to the additional information of image data representing the pressed predetermined button to generate a command signal corresponding to the additional information.

In addition, the system control circuitry 128 obtains, as terminal operation screen data, image data corresponding to the operation screen after the change, which is requested by the received command signal, and the additional information of the image data from the operation screen database stored in advance in the memory 127.

The operation screen after the change which is requested by the command signal is, for example, an initial screen immediately after a screen displaying an ultrasound image is switched to an operation screen for the operation of each function, an operation screen for the operation of a predetermined function different from the initial screen, or an operation screen, of operation screens, on which a predetermined function button is highlighted.

Note that the system control circuitry 128 may finely modify obtained terminal operation screen data in accordance with the screen specifications of the terminal equipment 2.

The system control circuitry 128 transmits obtained terminal operation screen data to the operation screen encoding circuitry 129 (to be described later).

The parameter setting function 128-2 is a function of setting parameters for ultrasound image data to be transmitted from the ultrasound diagnostic apparatus 1 to the terminal equipment 2 (to be described later).

More specifically, with the parameter setting function 128-2, the system control circuitry 128 obtains a data size per predetermined ultrasound image frame generated by the display processing circuitry 126 of the ultrasound diagnostic apparatus 1, a display frame rate, and the predetermined compression ratio of ultrasound image data from the memory 127 while the ultrasound image data generated by the display processing circuitry 126 is displayed on the monitor 13. The system control circuitry 128 calculates an image data generation rate Ru based on the obtained data size per ultrasound image frame, display frame rate, and the compression ratio of ultrasound image data.

The system control circuitry 128 measures an image data transfer rate Rt of the communication line between the ultrasound diagnostic apparatus 1 and the terminal equipment 2. The image data transfer rate Rt is an effective transmission bit rate which can be used for data transfer through the communication line between the ultrasound diagnostic apparatus 1 and the terminal equipment 2. The system control circuitry 128 compares the calculated image data generation rate Ru with the measured image data transfer rate Rt. If the comparison result indicates that Ru is higher than Rt, the system control circuitry 128 changes a predetermined set value to make Ru equal to Rt after compression, that is, to further increase the compression ratio at the time of compression processing of ultrasound image data in the image encoding circuitry 130 (to be described later). Note that to change the predetermined set value to further increase the compression ratio is to further reduce the data size of data compressed at the compression ratio after the change. In contrast, if the comparison result indicates that Ru is equal to or less than Rt, the system control circuitry 128 does not change the predetermined compression ratio.

According to the above description, the system control circuitry 128 controls only a compression ratio. However, as will be described later, since large-capacity DICOM (Digital Imaging and Communication in Medicine) data and the like are transferred between the ultrasound diagnostic apparatus 1 and a network system such as a PACS, only control on a compression ratio does not sometimes sufficiently guarantee the real-time performance of ultrasound image data transmission from the ultrasound diagnostic apparatus 1 to the terminal equipment 2. In such a case, the system control circuitry 128 controls the terminal display frame rate in addition to or instead of control on the compression ratio. That is, the system control circuitry 128 executes the parameter setting function 128-2 to calculates an image generation rate Rum based on the data size per ultrasound image frame, the display frame, and high compression ratio corresponding to the allowable limit value of ultrasound image data, which are obtained from the memory 127. The high compression ratio corresponding to the allowable limit value indicates, for example, the highest compression ratio set in accordance with the minimum image quality allowed with respect to a predetermined ultrasound image. In addition, the system control circuitry 128 compares the calculated image generation rate Rum with the measured image data transfer rate Rt. If the comparison result indicates that Rum is equal to or less than Rt, the system control circuitry 128 changes a predetermined set value to make Ru equal to Rt after compression, that is, to further increase the compression ratio at the time of compression processing of ultrasound image data in the image encoding circuitry 130 (to be described later). If the comparison result indicates that Rum is higher than Rt, for example, the system control circuitry 128 sets the compression ratio at the time of compression processing of ultrasound image data in the image encoding circuitry 130 (to be described later) to the allowable limit value. If the comparison result indicates that Rum is higher than Rt, for example, the system control circuitry 128 decreases the terminal display frame rate below a preset value as well as setting the compression ratio.

Alternatively, the system control circuitry 128 may perform, for example, parameter setting so as to partially cut the ultrasound image generated by the display processing circuitry 126 instead of or in addition to control on a compression ratio and a terminal display frame rate.

The SoftwareAP function 128-3 is a function of generating a virtual access point for wireless communication between the terminal equipment 2 and the ultrasound diagnostic apparatus 1. More specifically, with the SoftwareAP function 128-3, the system control circuitry 128 generates a virtual access point by controlling the communication interface circuitry 131 when a second console start button is pressed. The second console start button is provided at a predetermined position on the touch panel of the input interface circuitry 14 of the ultrasound diagnostic apparatus 1. Note that the second console start button may be provided as one of a plurality of switch buttons of the panel switches of the input interface circuitry 14 (to be described later).

In addition, the system control circuitry 128 sets an SSID (Service Set Identifier) and a password when generating this access point. An SSID and a password may be manually set by the operator 3 via the input interface circuitry 14 or may be set automatically. Note that a password is a one-time password updated for each communication connection between the ultrasound diagnostic apparatus 1 and the terminal equipment 2 or periodically. A one-time password is a password generated based on, for example, a mathematical algorithm or the like.

In addition, the system control circuitry 128 is communicably connected to the terminal equipment 2 via the communication interface circuitry 131 based on preset connection information. Note that in this embodiment, authentication concerning communication connected between the ultrasound diagnostic apparatus 1 and the terminal equipment 2 is automatically performed based on preset connection information. The preset connection information is information necessary for communication connection, such as the SSID of a generated access point, a password necessary for connection, and the MAC addresses (Media Access Control addresses) of the ultrasound diagnostic apparatus 1 and the terminal equipment 2.

Note that the system control circuitry 128 may establish communication connection upon receiving a communication connection request from the terminal equipment 2. In this case, authentication processing is performed on the ultrasound diagnostic apparatus 1 side by determining the authentication of a password or the like input in the terminal equipment 2.

In addition, after the establishment of communication connection to the terminal equipment 2, the system control circuitry 128 issues a password input request to the terminal equipment 2 to operate the ultrasound diagnostic apparatus 1 from the terminal equipment 2 via the communication interface circuitry 131.

The authentication information display function 128-4 is a function of presenting identification information necessary for the terminal equipment 2 to operate the ultrasound diagnostic apparatus 1. More specifically, with the authentication information display function 128-4, the system control circuitry 128 displays the identification information on the monitor 13. Note that the display place of the identification information may be any preset position on the monitor 13. Identification information includes, for example, the SSID and the password set by the SoftwareAP function 128-3. Of the identification information, the password is an enumeration of preset characters, symbols, and numerals for authenticating the operator 3 whether he/she is an authentic user allowed to directly perform a predetermined operation concerning the ultrasound diagnostic apparatus 1 from the terminal equipment 2. This password may differ from the password set by the SoftwareAP function 128-3. In this case, the password is a one-time password updated for each communication connection between the ultrasound diagnostic apparatus 1 and the terminal equipment 2 or periodically. Although a password has been exemplified as identification information necessary for authentication, a predetermined ID and password different from an SSID may be used as identification information.

The authentication function 128-5 is a function of permitting a predetermined operation concerning the ultrasound diagnostic apparatus 1 upon authenticating response data which is transmitted from the terminal equipment 2 to the ultrasound diagnostic apparatus 1 in accordance with a password input request issued from the SoftwareAP function 128-3 to the terminal equipment 2. More specifically, with the authentication function 128-5, the system control circuitry 128 receives response data corresponding to a password input request from the terminal equipment 2 via the communication interface circuitry 131. The system control circuitry 128 compares the password included in the received response data with the password displayed by the authentication information display function 128-4. If the password included in the response data matches the password displayed by the authentication information display function 128-4, the system control circuitry 128 permits the operator 3 to directly perform a predetermined operation concerning the ultrasound diagnostic apparatus 1 from the terminal equipment 2.

The basic control function 128-6 is a function of controlling basic operations such as the input/output operation of the ultrasound diagnostic apparatus 1. More specifically, with the basic control function 128-6, the system control circuitry 128 receives, for example, a command signal via the input interface circuitry 14. The command signal is a signal for instructing to execute a predetermined function of the ultrasound diagnostic apparatus 1. The command signal includes a predetermined execution command. If the command signal indicates a predetermined command for operating predetermined circuitry of the ultrasound diagnostic apparatus 1, the system control circuitry 128 controls the predetermined circuitry in accordance with the purpose of the predetermined command. In addition, the system control circuitry 128 displays an ultrasound diagnostic image, an operation screen, and the like on the monitor 13 via the display processing circuitry 126.

The operation screen encoding circuitry 129 is a processor which compresses terminal operation screen data obtained by the operation screen generating function 128-1 of the system control circuitry 128 under the control of the system control circuitry 128. Note that since an operation screen rarely changes moment to moment as a whole with respect to the time axis, the operation screen encoding circuitry 129 preferably uses a compression technique such as MPEG (Moving Picture Experts Group) which compresses an information amount by taking the difference between image data adjacent to each other on the time axis. In addition, the operation screen encoding circuitry 129 preferably uses a compression technique such as MPEG which compresses an information amount by taking the difference between the pieces of additional information of the image data adjacent to each other on the time axis. In this case, each frame includes image data and the additional information of the image data.

The image encoding circuitry 130 is a processor which compresses ultrasound image data generated by the display processing circuitry 126 under the control of the system control circuitry 128. Note that since a new ultrasound image needs to be always displayed with respect to the time axis, it is preferable to use a compression technique such as JPEG (Joint Photographic Expert Group) which can obtain a high compression ratio.

The communication interface circuitry 131 is a processor which controls communication connection and various types of data communications with the terminal equipment 2 via a communication line. The communication interface circuitry 131 has a builtin wireless LAN antenna. The communication interface circuitry 131 transmits terminal operation screen data compressed by the operation screen encoding circuitry 129 to the terminal equipment 2 via the communication line under the control of the system control circuitry 128. The communication interface circuitry 131 transmits image data compressed by the image encoding circuitry 130 to the terminal equipment 2 via the communication line under the control of the system control circuitry 128. In addition, the communication interface circuitry 131 receives a command signal transmitted by the terminal equipment 2 via the communication line under the control of the system control circuitry 128.

The input interface circuitry 14 includes a trackball, panel switches, a mouse, a keyboard, a touch pad which performs an input operation when the operation surface is touched, and a touch panel, which are used to input various types of instructions, conditions, an instruction to set an ROI (Region Of Interest), and various types of image quality condition setting instructions from the operator 3 to the apparatus main body 12. The touch panel is a panel obtained by integrating a display screen with a touch pad. The input interface circuitry 14 is connected to the system control circuitry 128 of the apparatus main body 12, and outputs an input operation received from the operator to the control circuitry upon converting the operation into an electrical signal. Note that in this specification, the input interface circuitry 14 is not limited to the one including physical operation components such as a mouse and a keyboard. For example, the input interface circuitry also includes electrical signal processing circuitry which receives an electrical signal corresponding to an input operation from an external input device provided separately from the apparatus and outputs the electrical signal to the system control circuitry 128 of the apparatus main body 12.

The terminal equipment 2 is equipment which is communicably connected to the ultrasound diagnostic apparatus 1 via a communication line R, and can be used separately from the ultrasound diagnostic apparatus 1. The terminal equipment 2 may be a tablet type information terminal or a portable information terminal such as a smartphone. This embodiment will exemplify a tablet type information terminal as the terminal equipment 2.

Figure 2:
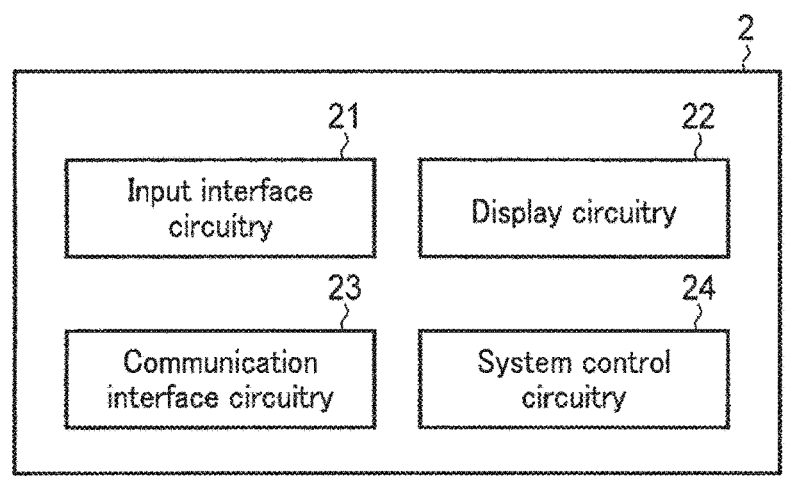
FIG. 2 is a block diagram showing the arrangement of terminal equipment according to the embodiment.

FIG. 2 is a block diagram showing an example of the arrangement of the terminal equipment 2 according to this embodiment. As shown in FIG. 2, the terminal equipment 2 includes the input interface circuitry 21, the display circuitry 22, communication interface circuitry 23, and system control circuitry 24.

The input interface circuitry 21 may be a touch panel stacked on the display screen of the display circuitry 22 or the like. This circuitry receives an operation instruction from the operator 3 and outputs the instruction to the system control circuitry 24.

The display circuitry 22 includes a general display output apparatus such as a liquid crystal display or OLED (Organic Light Emitting Diode) display. The display circuitry 22 displays an operation screen and various types of images for operating the ultrasound diagnostic apparatus 1 under the control of the system control circuitry 24.

The communication interface circuitry 23 is a processor which is communicably connected to the ultrasound diagnostic apparatus 1 via a communication line under the control of the system control circuitry 24 and transmits/receives data.

The system control circuitry 24 is a processor which controls, for example, each constituent circuitry of the terminal equipment 2. The system control circuitry 24 functions as the main unit of the terminal equipment 2. More specifically, the system control circuitry 24 controls the display circuitry 22 to display at least one of an operation screen and an ultrasound image, which are transmitted from the ultrasound diagnostic apparatus 1, and an image of the panel switches of the input interface circuitry 14. In addition, the system control circuitry 24 receives ultrasound diagnostic image data and terminal operation screen data from the ultrasound diagnostic apparatus 1 via the communication interface circuitry 23. Note that the received ultrasound diagnostic image data and terminal operation screen data are only temporarily used and are not stored in the terminal equipment 2. In addition, the system control circuitry 24 receives image data representing an image of the panel switches of the input interface circuitry 14 from the ultrasound diagnostic apparatus 1 via the communication interface circuitry 23.

The system control circuitry 24 also receives an operation instruction from the operator 3 via the input interface circuitry 21. When the operator 3 presses a predetermined button on the touch panel of the input interface circuitry 21, the system control circuitry 24 refers to the additional information of image data representing the pressed predetermined button to generate a command signal corresponding to the additional information. The command signal is a signal for instructing to change the operation screen displayed on the touch panel of the input interface circuitry 21 of the terminal equipment 2 to a predetermined operation screen. The command signal is also a signal for instructing the ultrasound diagnostic apparatus 1 to execute a predetermined function. The command signal includes at least one of information representing an operation screen after the change which is provided to change the operation screen displayed on the touch panel of the input interface circuitry 21 to a predetermined operation screen and an execution command for instructing the ultrasound diagnostic apparatus 1 to execute a predetermined function. The system control circuitry 24 controls the communication interface circuitry 23 to transmit a command signal corresponding to a received operation instruction to the ultrasound diagnostic apparatus 1.

Figure 3:
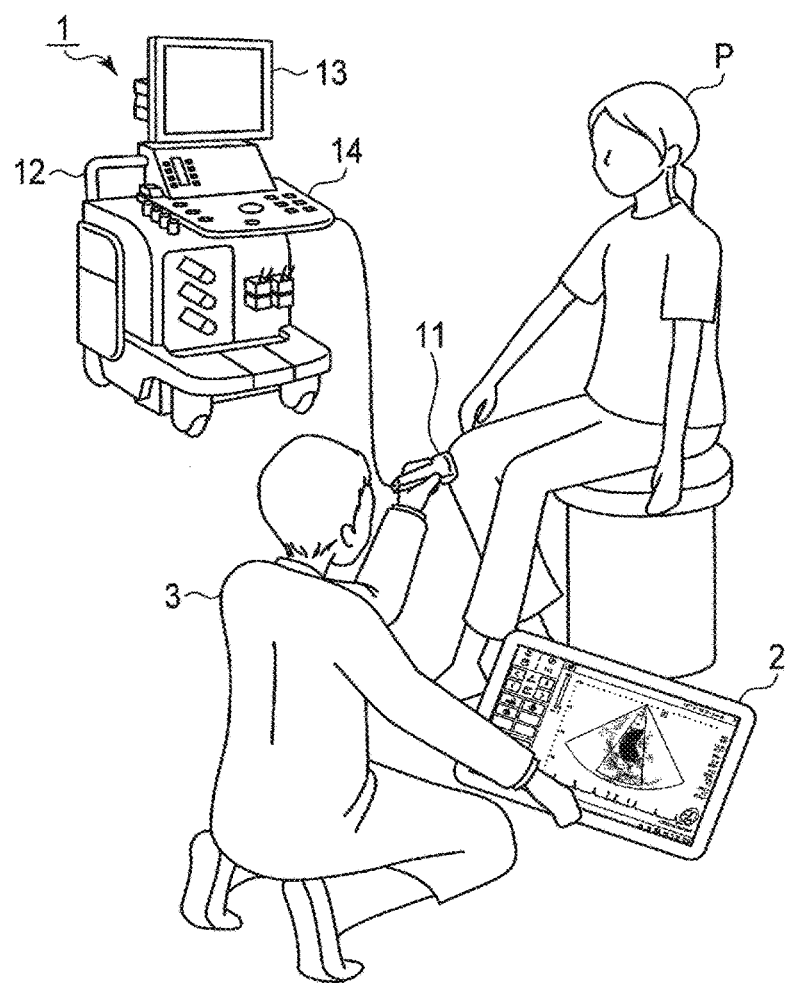
FIG. 3 is a perspective view showing the positional relationship between an apparatus main body, an ultrasound probe, a monitor, input interface circuitry, terminal equipment, an operator, and an object according to the embodiment.

The operation of the first embodiment will be described next. FIG. 3 is a perspective view showing an example of the positional relationship between the apparatus main body 12 according to this embodiment, the ultrasound probe 11, the monitor 13, the input interface circuitry 14, the terminal equipment 2, the operator 3, and an object P. The following will describe an authentication procedure by which the terminal equipment 2 operates the ultrasound diagnostic apparatus 1, an ultrasound image data transfer procedure by which the ultrasound diagnostic apparatus 1 transfers ultrasound image data to the terminal equipment 2 based on an operation instruction from the terminal equipment 2, and an operation screen data transfer procedure by which the ultrasound diagnostic apparatus 1 transfers operation screen data to the terminal equipment 2 based on an operation instruction from the terminal equipment 2.

(1) Authentication Procedure

Figure 4:
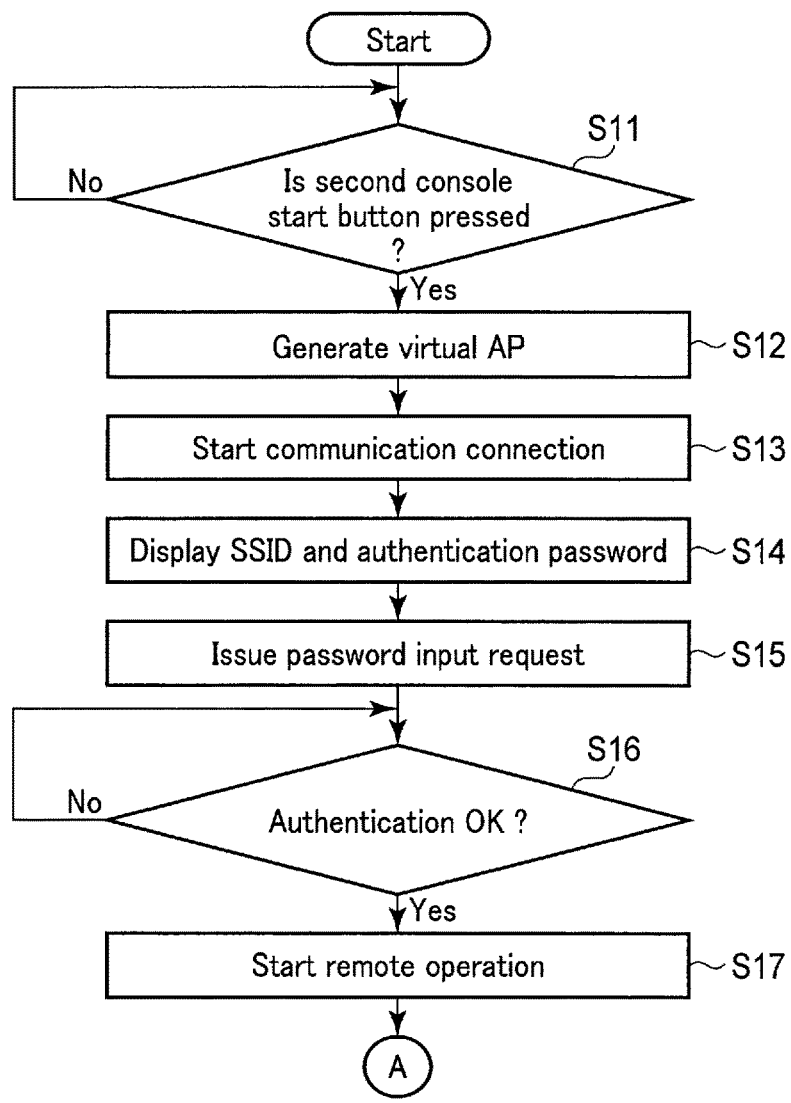
FIG. 4 is a flowchart showing a procedure for authentication processing performed by various functions of system control circuitry according to the embodiment.

FIG. 4 is a flowchart showing an example of a procedure for authentication processing performed by the respective functions of the system control circuitry 128 according to this embodiment.

First of all, the system control circuitry 128 executes the SoftwareAP function 128-3 to stand by until the second console start button is pressed (step S11).

When the second console start button is pressed, the system control circuitry 128 generates a virtual access point (step S12). In this case, an SSID and a password are set.

After access point generation in step S12, the system control circuitry 128 is communicably connected to the terminal equipment 2 via the communication interface circuitry 131 based on preset connection information (step S13). Note that authentication concerning communication connection between the ultrasound diagnostic apparatus 1 and the terminal equipment 2 is automatically performed based on the preset connection information.

Figure 4A:
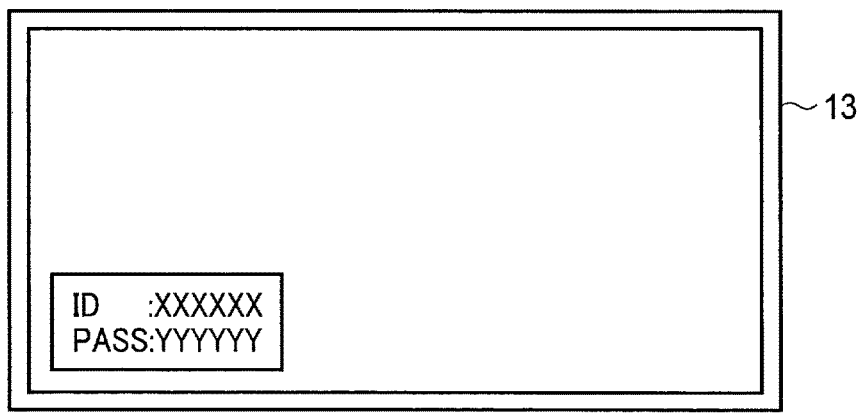
FIG. 4A is a view showing authentication information displayed on the monitor of the ultrasound diagnostic apparatus according to the embodiment.

The system control circuitry 128 then executes the authentication information display function 128-4 to display the SSID and the password set in step S11 on the monitor 13 (step S14). The system control circuitry 128 displays the SSID and the password on the lower left of the display portion of the monitor 13, as shown in, for example, FIG. 4A.

The system control circuitry 128 executes the SoftwareAP function 128-3 to issue a password input request to the terminal equipment 2 via the communication interface circuitry 131 upon establishment of communication connection to the terminal equipment 2 (step S15).

The system control circuitry 128 compares the password included in response data corresponding to the password input request, which is sent from the terminal equipment 2, with the password displayed by the authentication information display function 128-4 in step S14 (step S16). If the password included in the response data matches the password displayed by the authentication information display function 128-4 (YES in step S16), the system control circuitry 128 permits the operator 3 to directly perform a predetermined remote operation concerning the ultrasound diagnostic apparatus 1 from the terminal equipment 2 (step S17). Note that if the password included in the response data does not match the password displayed by the authentication information display function 128-4 (NO in step S16), the system control circuitry 128 generates password input request data again and transmits the generated password input request data to the terminal equipment 2 via the communication interface circuitry 131. If password mismatching has occurred a predetermined number of times, the system control circuitry 128, for example, locks subsequent processing.

(2) Image Data Transfer Procedure

The system control circuitry 128 transfers ultrasound image data from the ultrasound diagnostic apparatus 1 to the terminal equipment 2 upon controlling the compression ratio. The system control circuitry 128 also transfers ultrasound image data from the ultrasound diagnostic apparatus 1 to the terminal equipment 2 upon controlling the compression ratio and the terminal display frame rate.

(2-1) Image Data Transfer Based on Compression Ratio Control

Figure 5:
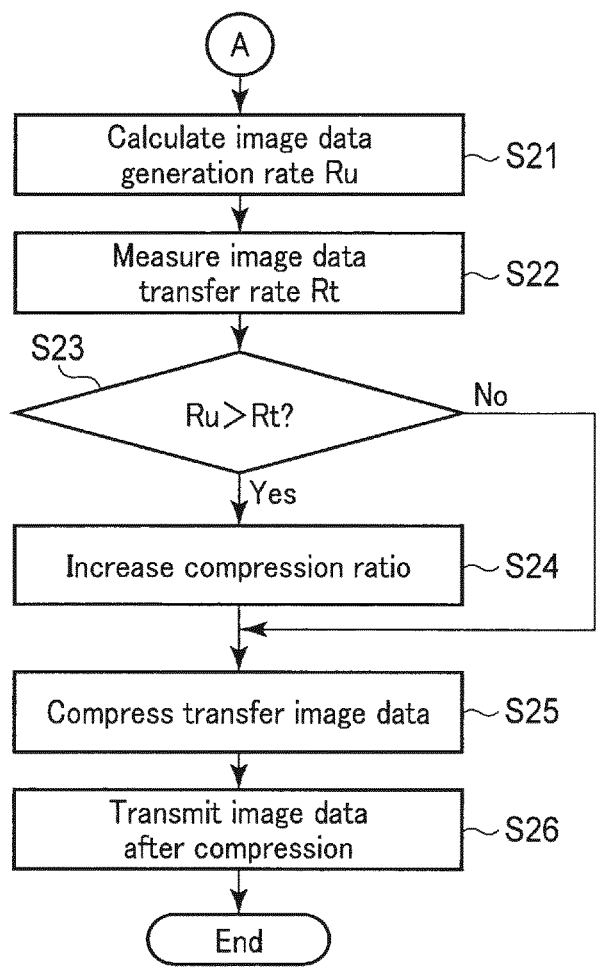
FIG. 5 is a flowchart showing a procedure for transferring ultrasound image data from the ultrasound diagnostic apparatus to the terminal equipment by controlling a compression ratio.

FIG. 5 is a flowchart showing a procedure for transferring ultrasound image data from the ultrasound diagnostic apparatus 1 to the terminal equipment 2 upon controlling the compression ratio.

First of all, the system control circuitry 128 executes the parameter setting function 128-2 to calculate an image data generation rate Ru based on a predetermined data size per ultrasound image frame generated by the display processing circuitry 126 of the ultrasound diagnostic apparatus 1, a display frame rate, and the predetermined compression ratio of ultrasound image data, which are stored in the memory 127 (step S21).

The system control circuitry 128 measures an image data transfer rate Rt of a communication line between the ultrasound diagnostic apparatus 1 and the terminal equipment 2 (step S22).

The system control circuitry 128 then compares the calculated image data generation rate Ru with the measured image data transfer rate Rt (step S23).

If the comparison result indicates that Ru is higher than Rt (YES in step S23), the system control circuitry 128 changes the predetermined set value to make Ru equal to Rt after compression, that is, to increase the predetermined compression ratio of the transfer image data (step S24).

The system control circuitry 128 then controls the image encoding circuitry 130 to compress the ultrasound image data generated by the display processing circuitry 126 based on the compression ratio set in step S25 (step S25). If the comparison result indicates that Ru is higher than Rt (NO in step S23), the system control circuitry 128 compresses the ultrasound image data generated by the display processing circuitry 126 at the predetermined compression ratio without changing the compression ratio.

The system control circuitry 128 then controls the communication interface circuitry 131 to transmit the compressed ultrasound image data to the terminal equipment 2 (step S26).

Figure 6:
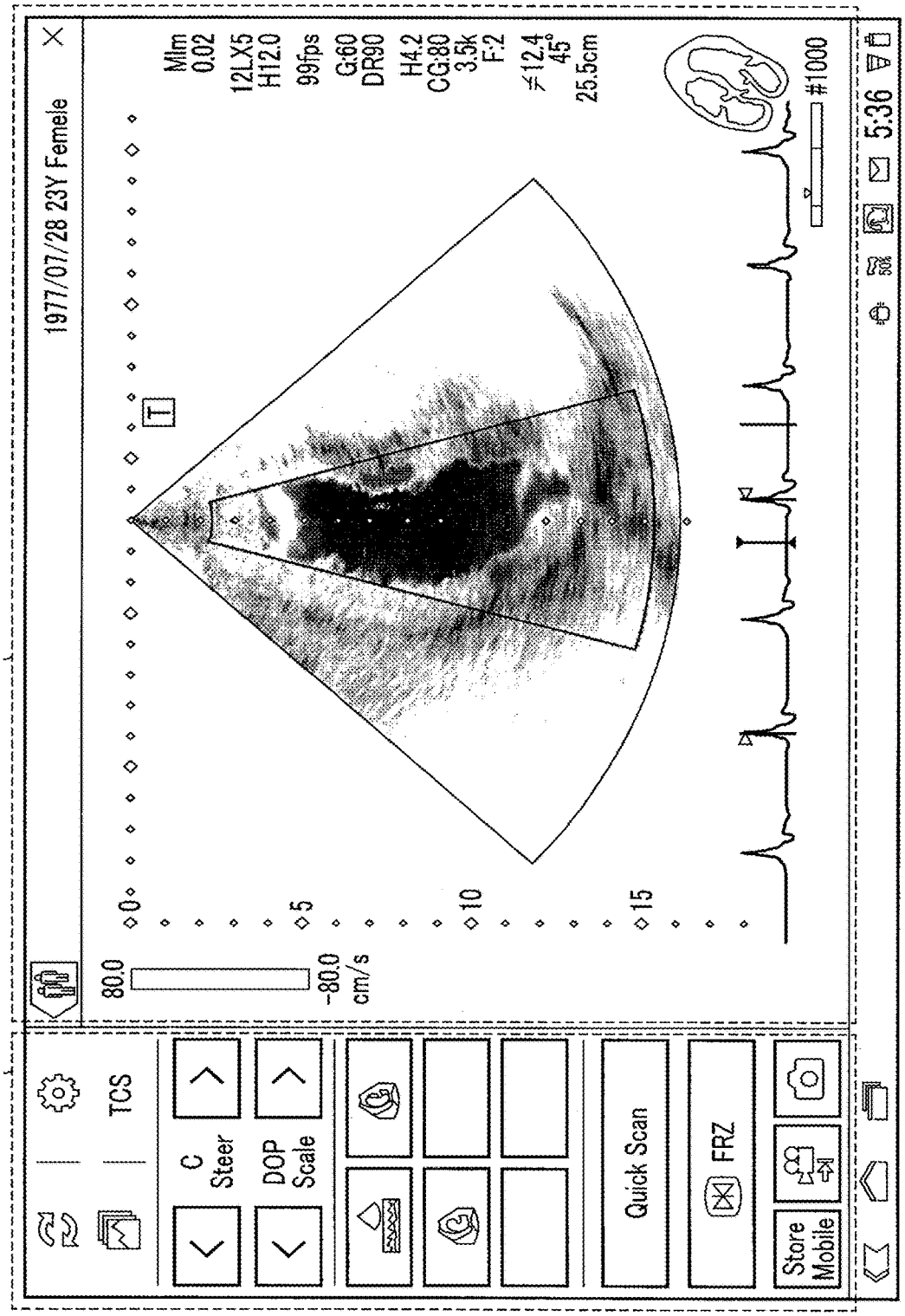
FIG. 6 is a view showing an image displayed on the display circuitry of the terminal equipment according to the embodiment.

FIG. 6 is a view showing an example of an image displayed on the display circuitry 22 of the terminal equipment 2. The image displayed in FIG. 6 includes an ultrasound image 221 and a panel switch image 213 of the input interface circuitry 14 of the ultrasound diagnostic apparatus 1. The ultrasound image 221 is displayed based on the ultrasound image data compressed by the image encoding circuitry 130. The panel switch image 213 is based on the panel switches of the input interface circuitry 14. The memory 127 of the ultrasound diagnostic apparatus 1 stores image data representing the panel switch image 213 and the additional information of the image data. The image data representing the panel switch image 213 and the additional information of the image data are read from the memory 127 into the terminal equipment 2 at the timing of step S17, that is, when it is permitted to directly perform a predetermined remote operation concerning the ultrasound diagnostic apparatus 1 from the terminal equipment 2.

The image data representing the panel switch image 213 and the additional information of the image data which are read into the terminal equipment 2 are edited at a predetermined timing based on an edit instruction notified from the ultrasound diagnostic apparatus 1 to the terminal equipment 2. More specifically, for example, the function information included in the additional information of the image data representing the panel switch image 213 is changed. In addition, in the ultrasound diagnostic apparatus 1, when the image data representing the panel switch image 213 is updated, the update content may be notified from the ultrasound diagnostic apparatus 1 to the terminal equipment 2, and the terminal equipment 2 may update the image data representing the panel switch image 213 based on the notified update content.

The panel switch image 213 may be displayed simultaneously with or independently of an operation screen and/or an ultrasound image transmitted by the ultrasound diagnostic apparatus 1.

Note that a control parameter to be controlled when YES is obtained in step S23 may be a terminal display frame rate instead of a compression ratio.

Figure 7:
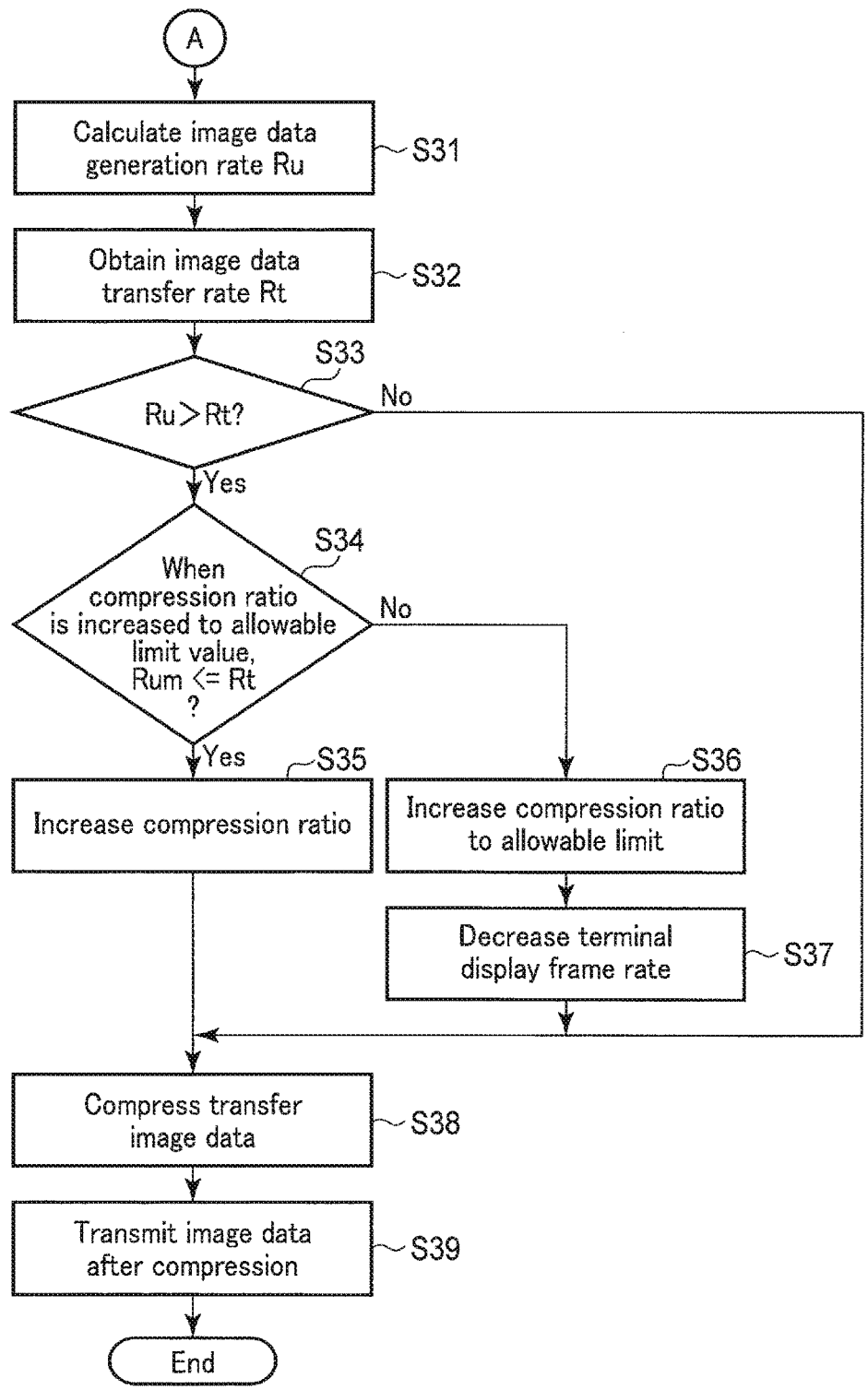
FIG. 7 is a flowchart showing a procedure for transferring ultrasound image data from the ultrasound diagnostic apparatus to the terminal equipment while controlling a compression ratio and a terminal display frame rate.

(2-2) Image Data Transfer Based on Control of Compression Ratio and Terminal Display Frame Rate FIG. 7 is a flowchart showing a procedure for transferring ultrasound image data from the ultrasound diagnostic apparatus 1 to the terminal equipment 2 upon controlling the compression ratio and the terminal display frame rate. When transferring large-capacity DICOM data or the like between the ultrasound diagnostic apparatus 1 and a network system such as a PACS, the apparatus load of the ultrasound diagnostic apparatus 1 increases. This increase in apparatus load is a cause of reduction in the effective transfer rate of communication between the ultrasound diagnostic apparatus 1 and the terminal equipment 2. When performing wireless communication between the ultrasound diagnostic apparatus 1 and a network system such as a PACS, in particular, a remarkable reduction in the effective transfer rate of communication sometimes occurs between the ultrasound diagnostic apparatus 1 and the terminal equipment 2. In this case, ultrasound image data is transferred upon controlling of the terminal display frame rate in addition to the compression ratio.

First of all, the system control circuitry 128 executes the parameter setting function 128-2 to calculate the image data generation rate Ru based on the predetermined data size per ultrasound image frame generated by the display processing circuitry 126 of the ultrasound diagnostic apparatus 1, the display frame rate, and the predetermined compression ratio of ultrasound image data, which are stored in the memory 127 (step S31).

The system control circuitry 128 measures the image data transfer rate Rt of the communication line between the ultrasound diagnostic apparatus 1 and the terminal equipment 2 (step S32).

The system control circuitry 128 compares the image data generation rate Ru with the image data transfer rate Rt (step S33).

If the comparison result indicates that Ru is higher than Rt (YES in step S33), the system control circuitry 128 calculates the image data generation rate Rum when the image data is compressed at a high compression ratio corresponding to an allowable limit value, and compares the calculated image data generation rate Rum with the image data transfer rate Rt (step S34).

If the comparison result indicates that Rum is equal to or less than Rt (YES in step S34), the system control circuitry 128 changes a predetermined set value to make Ru equal to Rt after compression, that is, to further increase the preset compression ratio of the transfer image data (step S35).

If the comparison result indicates that Rum is higher than Rt (NO in step S34), the system control circuitry 128 sets the preset compression ratio of the transfer image data to the allowable limit value (step S36).

After step S36, the system control circuitry 128 reduces the terminal display frame below the preset value (step S37).

The system control circuitry 128 controls the image encoding circuitry 130 to compress the ultrasound image data generated by the display processing circuitry 126 at the compression ratio set in step S35 or S36 (step S38). Note that if the comparison result indicates that Ru is equal to or less than Rt (NO in step S33), the system control circuitry 128 compresses the ultrasound image data generated by the display processing circuitry 126 at the predetermined compression ratio without changing the compression ratio.

Finally, the system control circuitry 128 controls the communication interface circuitry 131 to transmit the compressed ultrasound image data to the terminal equipment 2 (step S39).

(3) Operation Screen Data Transfer Procedure

Figure 8:
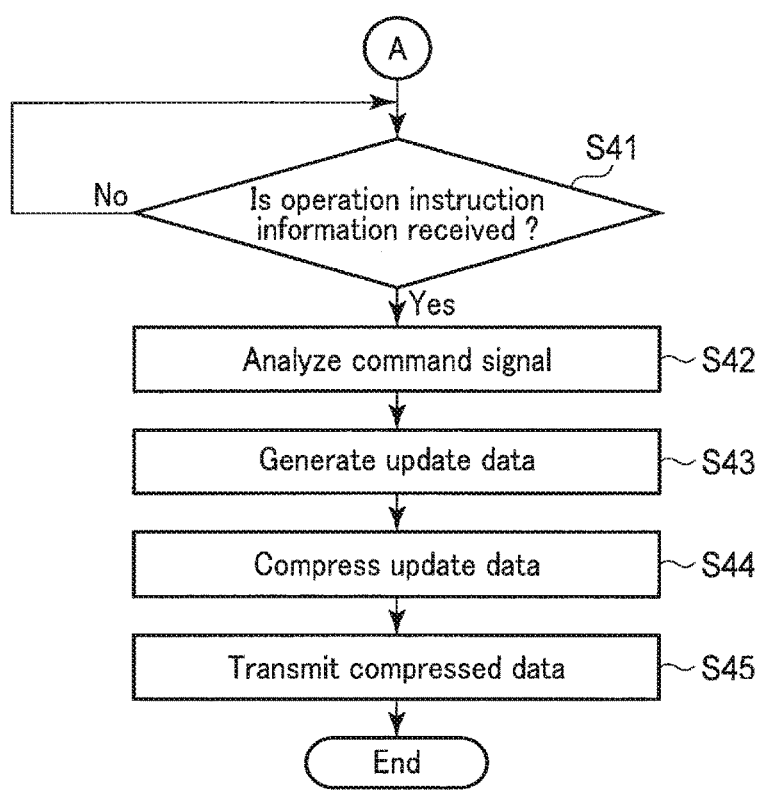
FIG. 8 is a flowchart showing a procedure for transferring operation screen data from the ultrasound diagnostic apparatus to the terminal equipment.
Figure 9:
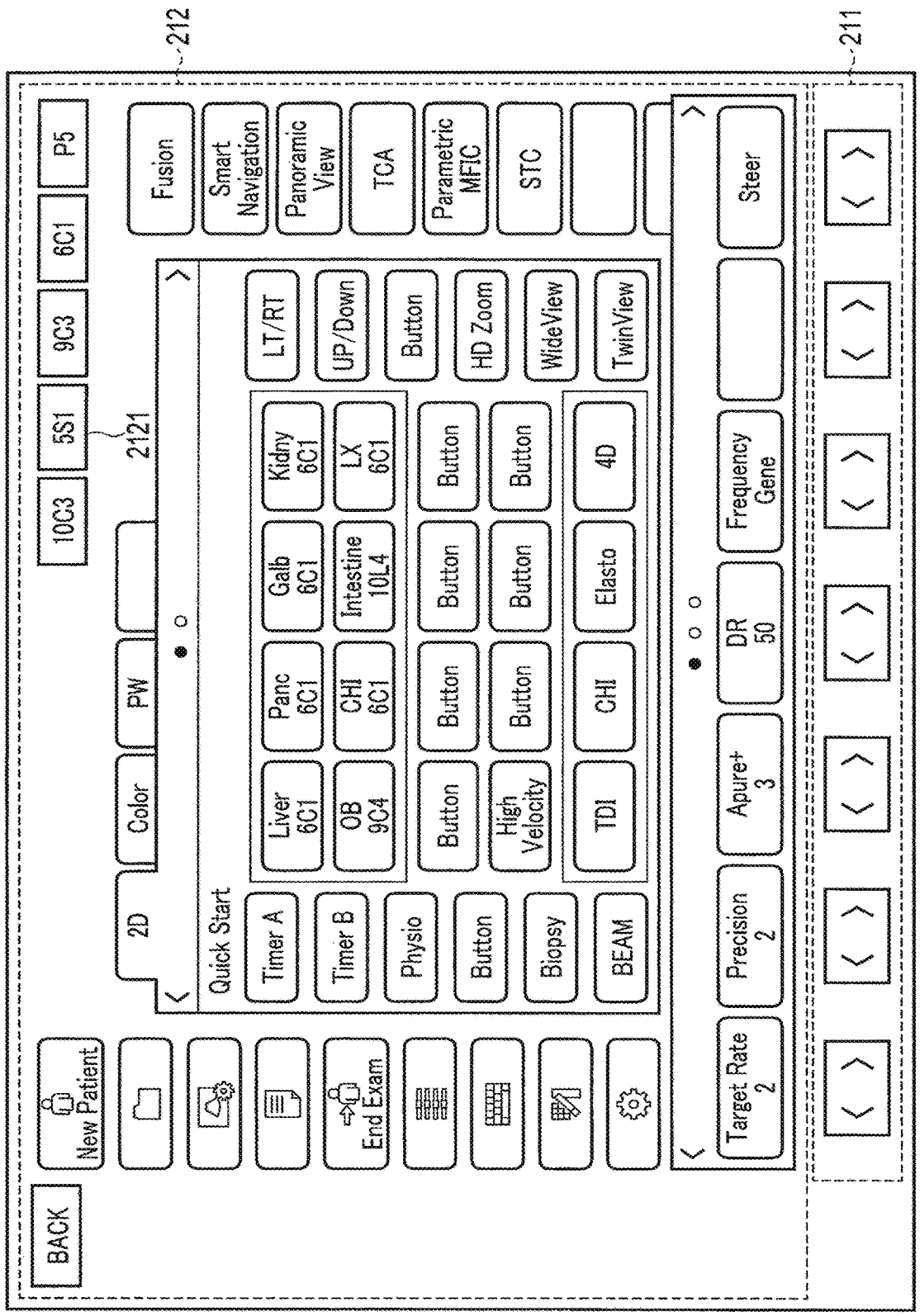
FIG. 9 is view showing an image displayed on a touch panel of input interface circuitry of the terminal equipment according to the embodiment.

The system control circuitry 128 transfers terminal operation screen data from the ultrasound diagnostic apparatus 1 to the terminal equipment 2. FIG. 8 is a flowchart showing an example of a procedure for transferring operation screen data from the ultrasound diagnostic apparatus 1 to the terminal equipment 2. FIG. 9 is a view showing an example of an image displayed on the touch panel of the input interface circuitry 21 of the terminal equipment 2. Referring to FIG. 9, a panel switch image 211 is an example of an image representing panel switches of the input interface circuitry 14 of the ultrasound diagnostic apparatus 1. The panel switch image 211 is displayed based on image data generated in advance based on panel switches of the input interface circuitry 14. The memory 127 of the ultrasound diagnostic apparatus 1 stores image data representing the panel switch image 211 and the additional information of the image data. The image data representing the panel switch image 211 and the additional information of the image data are read from the memory 127 into the terminal equipment 2, for example, at the timing in step S17, that is, when it is permitted to directly perform a predetermined remote operation concerning the ultrasound diagnostic apparatus 1 from the terminal equipment 2.

The image data representing the panel switch image 211 and the additional information of the image data which are read into the terminal equipment 2 are edited at a predetermined timing based on an edit instruction notified from the ultrasound diagnostic apparatus 1 to the terminal equipment 2. More specifically, for example, the function information included in the additional information of the image data representing the panel switch image 211 is changed. In addition, in the ultrasound diagnostic apparatus 1, when the image data representing the panel switch image 211 is updated, the update content may be notified from the ultrasound diagnostic apparatus 1 to the terminal equipment 2, and the terminal equipment 2 may update the image data representing the panel switch image 211 based on the notified update content.

In addition, the panel switch image 211 may be displayed simultaneously with or independently of an operation screen and/or an ultrasound image transmitted by the ultrasound diagnostic apparatus 1. In addition, a touch panel image 212 is an example of an image representing the touch panel of the input interface circuitry 14 of the ultrasound diagnostic apparatus 1. The flowchart shown in FIG. 8 will be described below by exemplifying a case in which a function button 2121 shown FIG. 9 is pressed. Note that operation screen data transfer processing is started in response to the pressing of a TCS (Touch Command Screen) button included in the panel switch image 213 shown in FIG. 6.

First of all, the system control circuitry 128 executes the operation screen generating function 128-1 to stand by until a command signal is notified from the terminal equipment 2 via the communication interface circuitry 131 (step S41).

Upon notification of the command signal from the terminal equipment 2, the system control circuitry 128 refers to the notified command signal to perform analysis to determine which one of a plurality of image data and which one of the pieces of additional information of the image data, which are included in the operation screen database stored in advance in the memory 127, are required as update information (step S42).

Figure 10:
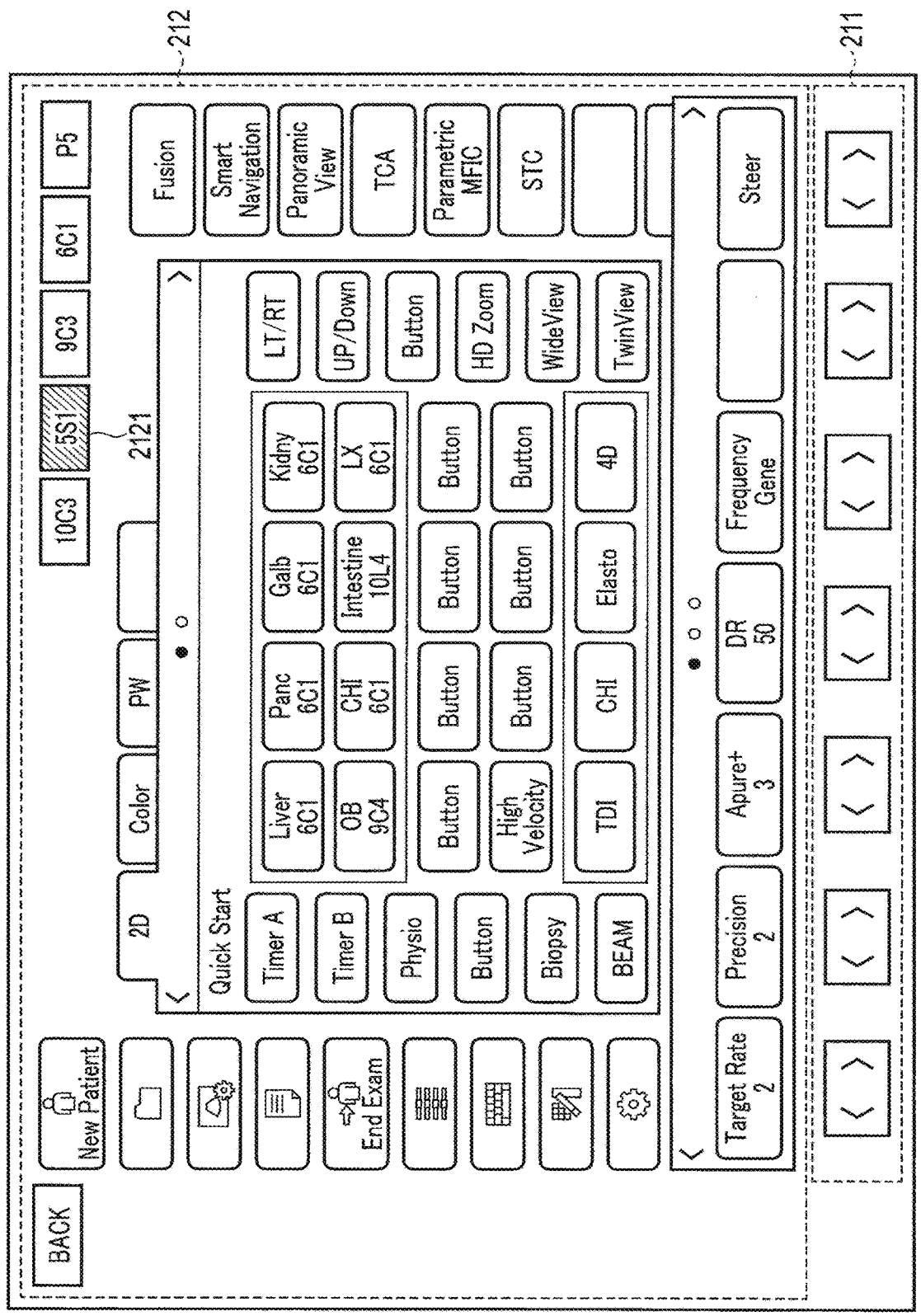
FIG. 10 is a view showing an image displayed on the touch panel of input interface circuitry of the terminal equipment according to the embodiment.

The system control circuitry 128 obtains, as terminal operation screen data, the image data and the additional information of the image data which are determined to be required as update information as a result of the analysis in step S42 (step S43). More specifically, the system control circuitry 128 obtains operation screen data representing the operation screen shown in FIG. 10 on which the function button 2121 on the operation screen shown in FIG. 9 is highlighted.

The system control circuitry 128 controls the operation screen encoding circuitry 129 to compress the obtained terminal operation screen data (step S44). For example, the system control circuitry 128 compresses an information amount by taking the difference between the terminal operation screen data representing the operation screen shown in FIG. 9 and the terminal operation screen data representing the operation screen shown in FIG. 10. Alternatively, the system control circuitry 128 may compress the information amount by taking the difference between terminal operation screen data adjacent to each other on the time axis.

The system control circuitry 128 controls the communication interface circuitry 131 to transmit the compressed terminal operation screen data to the terminal equipment 2 (step S45).

According to the first embodiment, the ultrasound diagnostic apparatus 1 is wirelessly communicably connected to the terminal equipment 2. The system control circuitry 128 obtains terminal operation screen data, compresses the obtained terminal operation screen data, and wirelessly transmits the compressed terminal operation screen data to the terminal equipment 2. In addition, the system control circuitry 128 reads the panel switch images 211 and 213 stored in the memory 127 and stores the readout images in the terminal equipment 2 in advance. This allows the operator 3 to display, on the touch panel of the input interface circuitry 21 of the terminal equipment 2, an image representing an operation screen including an image of the panel switches of the input interface circuitry 14 of the ultrasound diagnostic apparatus 1 and an image of the touch panel of the input interface circuitry 14 of the ultrasound diagnostic apparatus 1.

The ultrasound diagnostic apparatus according to this embodiment allows the operator to perform an operation for image diagnosis even if it is difficult for the operator to directly operate the console of the diagnostic apparatus.

In addition, according to the first embodiment, the system control circuitry 128 transmits terminal operation screen data to the terminal equipment 2 every time the system control circuitry 128 receives the data. This makes it possible to sequentially display a new operation screen on the touch panel of the input interface circuitry 21 of the terminal equipment 2.

According to the first embodiment, the system control circuitry 128 controls the operation screen encoding circuitry 129 to compress obtained terminal operation screen data. In this case, the system control circuitry 128 compresses an information amount by taking the difference between terminal operation screen data adjacent to each other on the time axis. This makes it possible to suppress a communication data amount between the ultrasound diagnostic apparatus 1 and the terminal equipment 2.

According to the first embodiment, the system control circuitry 128 controls the communication interface circuitry 131 to start to transmit terminal operation screen data in response to the reception of a command signal from the terminal equipment 2 as a trigger. This makes it possible to display an operation screen corresponding to a request from the operator 3 on the touch panel of the input interface circuitry 21 of the terminal equipment 2.

According to the first embodiment, the system control circuitry 128 executes the authentication information display function 128-4 to display, for example, a preset SSID and password on the monitor 13. That is, only the operator who can directly see the ultrasound diagnostic apparatus 1 has an access authority. This can reduce the risk of communication connection and remote control by an unauthorized third person.

In addition, according to the first embodiment, a password used by the authentication function 128-5 of the system control circuitry 128 at the time of authentication is a one-time password updated for each communication connection request or periodically. This can reduce the risk of communication connection and remote control by an unauthorized third person.

Furthermore, according to the first embodiment, the system control circuitry 128 calculates the image data generation rate Ru. The system control circuitry 128 measures the image data transfer rate Rt of a communication line between the ultrasound diagnostic apparatus 1 and the terminal equipment 2. The system control circuitry 128 compares the calculated image data generation rate Ru with the measured image data transfer rate Rt. If the comparison result indicates that Ru is higher than Rt, for example, the system control circuitry 128 changes a predetermined set value to make Ru equal to Rt after compression, that is, to further increase the preset compression ratio of transfer image data. The system control circuitry 128 compresses the ultrasound image data generated by the display processing circuitry 126, and transmits the compressed ultrasound image data to the terminal equipment 2.

That is, the system control circuitry 128 transmits the ultrasound image data generated by the display processing circuitry 126 to the terminal equipment 2 without decreasing the frame rate of the ultrasound image represented by the ultrasound image data by reducing the image quality. This allows the operator 3 to check an ultrasound image in real time on the terminal equipment 2 even if the acoustic frame rate of the ultrasound diagnostic apparatus 1 is high and the calculated image data generation rate Ru is higher than the measured image data transfer rate Rt.

Other Embodiments

Note that the present invention is not limited to the above embodiment. For example, according to the first embodiment, the memory 127 stores an operation screen database representing operation screens which are displayed on the touch panel of the input interface circuitry 21 of the terminal equipment 2 and used by the operator 3 to operate the ultrasound diagnostic apparatus 1 from the terminal equipment 2. However, this is not exhaustive. For example, the memory 127 may store an operation screen database representing operation screens which are displayed on the touch panel of the input interface circuitry 14 of the ultrasound diagnostic apparatus 1 and used by the operator 3 to operate the ultrasound diagnostic apparatus 1. In this case, the system control circuitry 128 generates terminal operation screen data by processing image data and the like obtained from the operation screen database in accordance with command signals from the terminal equipment 2. This allows the operator 3 to change an operation screen which is displayed on the touch panel of the input interface circuitry 21 of the terminal equipment 2 and used to operate the ultrasound diagnostic apparatus 1.

In addition, according to the first embodiment, the operation screen database includes a plurality of image data of various patterns corresponding to command signals which are used by the operator 3 to operate the ultrasound diagnostic apparatus 1 from the terminal equipment 2 and the additional information of the image data. However, this is not exhaustive. For example, the memory 127 may store image data representing operation screens of various patterns corresponding to command signals from the terminal equipment 2 upon dividing the data into a plurality of partial image data respectively representing press button images and the like. In addition, the memory 127 stores placement information or the like each indicating a specific position on an image representing an operation screen including given partial image represented by the partial image data at which the image is placed. In this case, the system control circuitry 128 executes the operation screen generating function 128-1 to generate terminal operation screen data corresponding to a command signal by combining a plurality of partial image data.

In addition, according to the first embodiment, when the comparison result in step S23 in FIG. 5 indicates that Ru is equal to or less than Rt, the system control circuitry 128 does not change the predetermined compression ratio. Furthermore, according to the first embodiment, when the comparison result in step S33 in FIG. 6 indicates that Ru is equal to or less than Rt, the system control circuitry 128 does not change the predetermined compression ratio. However, this is not exhaustive. That is, the system control circuitry 128 may change the predetermined set value to make Ru equal to Rt after compression, that is, to further decrease the preset compression ratio of transfer image data. This makes it possible to bring the quality of an image represented by transfer image data close to that of an image represented by ultrasound image data generated by the display processing circuitry 126.

Furthermore, in the first embodiment, the display frames of ultrasound images generated by the display processing circuitry 126 may be generated based on, for example, image data generated by periodic scanning on a two-dimensional area using a one-dimensional array probe or may be generated based on image data generated by performing rendering processing or MPR processing for volume data generated by periodic scanning on a three-dimensional area using a two-dimensional array probe.

Moreover, in the first embodiment, image data representing the panel switch image 211 and the additional information of the image data and image data representing the panel switch image 213 and the additional information of the image data may be read into the terminal equipment 2, together with a client application at the time of the installation of the client application in the terminal equipment 2.

The term "processor" used in the above description means circuitry such as a CPU (Central Processing Unit), GPU (Graphics Processing Unit), ASIC (Application Specific Integrated Circuit), programmable logic device (e.g., an SPLD (Simple Programmable Logic Device), a CPLD (Complex Programmable Logic Device), or an FPGA (Field Programmable Gate Array)), or the like. The processor implements functions by reading programs stored in the memory and executing them. Note that it is possible to directly incorporate programs in the circuitry of the processor instead of storing them in the memory. In this case, the processor implements functions by reading programs incorporated in the circuitry and executing them. Note that each processor in this embodiment may be formed as one processor by combining a plurality of independent circuits to implement functions as well as being formed as single circuitry for each processor. In addition, a plurality of constituent elements in FIGS. 1 and 2 may be integrated into one processor to implement its function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A method, comprising:
    wirelessly transmitting, by an ultrasound diagnostic apparatus including imaging means for imaging an inside of an object, screen data to a portable information terminal wirelessly communicably connected to the ultrasound diagnostic apparatus, wherein the screen data is data for a display device of the portable information terminal to display an operation screen for operating the imaging means, wherein the screen data for the display device of the portable information terminal to display the operation screen comprises, for each of respective plural virtual buttons on the operation screen, (a) data representing a shape of a respective physical function button arranged on a physical operation button arrangement section of the ultrasound diagnostic apparatus, (b) data indicating a location on the operation screen the respective virtual button is to be displayed, and (c) data indicating an imaging function to be executed by the imaging means in response to receiving an input operation on the respective virtual button by the operator, wherein the imaging function corresponds to the imaging function performed when the respective physical function button arranged on the physical operation button arrangement section of the ultrasound diagnostic apparatus is selected by the operator;
    causing, by the portable information terminal, the display device to display the operation screen based on the received screen data;
    causing, by the portable information terminal, the display device to graphically display based on the screen data representing the plural respective physical function buttons arranged on the operation button arrangement section, the operation screen including the respective plural virtual buttons having the shapes of the respective physical buttons and at the respective locations on the operation screen indicated by the location data of the screen data, the operation screen receiving the input operation by the operator for causing the imaging means to execute the function corresponding to the plural respective physical function buttons whereby the operating screen provides a virtual version of the plural respective physical function buttons of the operation button arrangement section physically on the ultrasound diagnostic device, the screen data being stored to the portable information terminal in advance;

causing the ultrasound diagnostic apparatus to wirelessly transmit updated screen data to the portable information terminal whenever the screen data is updated;

causing the portable information terminal to update the operation screen based on the updated screen data whenever newly receiving screen data from the ultrasound diagnostic apparatus via wireless communication;

wirelessly transmitting, to the ultrasound diagnostic apparatus by the portable information terminal, a command signal for operating the imaging means, the command signal corresponding to the function associated with screen data of the respective virtual button selected using the operation screen; and controlling, by the ultrasound diagnostic apparatus, the imaging means based on the received command signal.

2. The method of claim 1, further comprising editing the operation screen in accordance with an edit instruction from the medical diagnostic imaging apparatus.

3. The method of claim 1, wherein the operation screen corresponds to a first operation screen, and the method further comprises causing, by the portable information terminal, the display device to display the first operation screen, which is generated based on second operation screen data useable on a touch panel of the medical diagnostic imaging apparatus and including a second operation screen for reception of an operation from the operator.

4. The method of claim 3, further comprising causing, by the portable information terminal, the display device to display the first operation screen, which is generated by extracting part of the second operation screen.

5. The method of claim 1, wherein the operation screen corresponds to a first operation screen, and the method further comprises causing, by the portable information terminal, the display device to simultaneously display the operation screen and the operation screen.

6. The method of claim 1, wherein the operation screen corresponds to first operation screen, and the method further comprises causing, by the portable information terminal, the display device to separately display the first operation screen and the operation screen.

7. The method of claim 1, wherein the operation accepted by the input interface of the medical diagnostic imaging apparatus includes an image processing operation.

8. The method as claimed in claim 1, wherein the wirelessly transmitting, by a medical diagnostic imaging apparatus, and the wirelessly transmitting, to the medical diagnostic imaging apparatus by the portable information terminal, comprise wireless transmitting over a dedicated wireless network.

* * * * *